United States Patent
Raab

(10) Patent No.: US 6,856,882 B2
(45) Date of Patent: Feb. 15, 2005

(54) DEVICE FOR RECOGNIZING THE RISK OF AQUAPLANING WHICH CAN OCCUR DURING THE DRIVING OF A VEHICLE

(75) Inventor: Markus Raab, Kirchhardt (DE)

(73) Assignee: DaimlerChrysler AG, Stuttgart (DE)

( * ) Notice: Subject to any disclaimer, the term of this patent is extended or adjusted under 35 U.S.C. 154(b) by 91 days.

(21) Appl. No.: 10/182,868

(22) PCT Filed: Nov. 17, 2001

(86) PCT No.: PCT/EP01/13295

§ 371 (c)(1),
(2), (4) Date: Dec. 13, 2002

(87) PCT Pub. No.: WO02/46008

PCT Pub. Date: Jun. 13, 2002

(65) Prior Publication Data

US 2003/0101805 A1 Jun. 5, 2003

(30) Foreign Application Priority Data

Dec. 4, 2000 (DE) .......................... 100 60 333

(51) Int. Cl.$^7$ ................................................ B60L 3/00
(52) U.S. Cl. ............................. 701/70; 701/21; 440/1; 440/3; 440/6; 440/9; 440/38
(58) Field of Search ................................. 701/70, 1, 21, 701/36; 114/56.1; 440/1, 3, 9, 6, 38

(56) References Cited

U.S. PATENT DOCUMENTS 5,832,856 A * 11/1998 Giles ........................ 114/61.26
6,092,006 A * 7/2000 Dominke et al. .............. 701/1

FOREIGN PATENT DOCUMENTS

| DE | 31 19 153 A1 | 5/1981 |
| DE | 40 20 505 A1 | 1/1992 |
| DE | 43 29 745 C1 | 7/1994 |
| DE | 43 17 030 A1 C2 | 11/1994 |
| DE | 44 27 170 C1 | 10/1995 |

* cited by examiner

Primary Examiner—William A. Cuchlinski, Jr.
Assistant Examiner—Olga Hernandez
(74) Attorney, Agent, or Firm—Crowell & Moring LLP

(57) ABSTRACT

The device according to the invention relates to a device for detecting a risk of aquaplaning which arises during the driving mode of a vehicle. The device contains for this purpose first means which determine a first propulsion variable which describes the propulsion of the vehicle which is to be expected on the basis of the operating state of the engine and/or of the drive train. In addition the device contains second means which determine a second propulsion variable which describes the propulsion occurring during the driving mode of the vehicle and which arises due to the longitudinal acceleration acting on the vehicle. The presence of the risk of aquaplaning is inferred as a function of a deviation between the first propulsion variable and the second propulsion variable.

14 Claims, 2 Drawing Sheets

Figure 1:
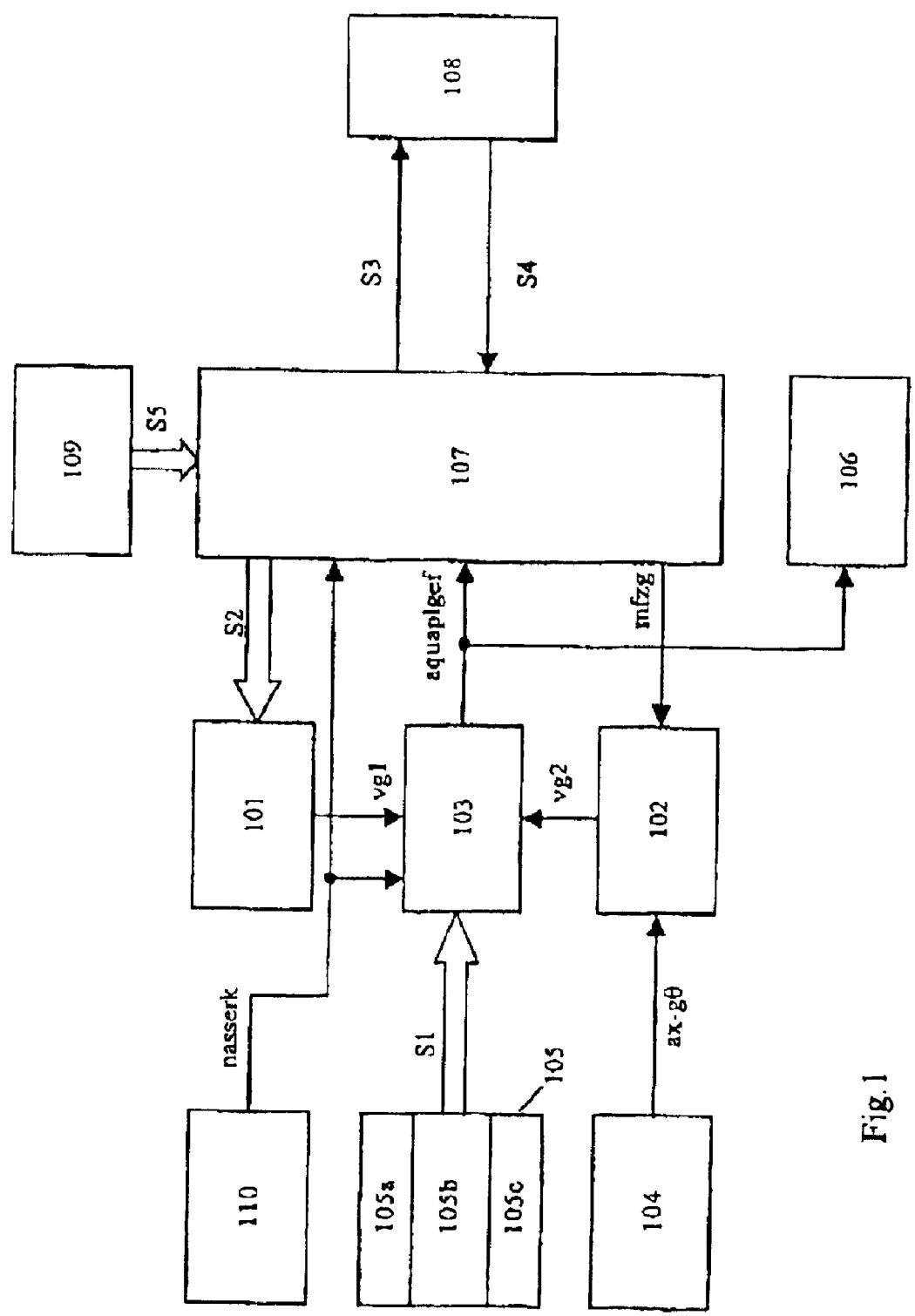

DEVICE FOR RECOGNIZING THE RISK OF AQUAPLANING WHICH CAN OCCUR DURING THE DRIVING OF A VEHICLE

The invention relates to a device for detecting a risk of aquaplaning which occurs during the driving mode of a vehicle. A wide range of modifications of such devices are known from the prior art.

DE 43 17 030 C2 discloses a method for detecting a driving state on a vehicle when the underlying surface is wet. For this purpose, a computer is supplied with the rotational speeds of the wheels, the velocity of the vehicle, the signal determined using a wetness sensor, and the external temperature. The velocities of the wheels are calculated from the rotational speeds of the wheels and the velocity of the vehicle. The slip values for the individual wheels are determined using the velocities of the wheels and the velocity of the vehicle. The signal of the wetness sensor is supplied, together with the slip values and the velocity of the vehicle, to a characteristic diagram computer. The characteristic diagram computer compares the incoming signals with a wetness characteristic diagram. A driving state evaluation is calculated from the wetness characteristic diagram and a coefficient-of-friction characteristic diagram which is related to the height of the water. The evaluation of the driving state is supplemented by the signals of the temperature sensor. When driving in wetness, the evaluation of the driving state can thus be calculated and the degree of risk of aquaplaning can be indicated to the driver by means of a water-height and aquaplaning display, a possible slip and coefficient-of-friction display and by means of a temperature display. Furthermore the values from the evaluation of the driving state are available in order to bring about counter measures against aquaplaning.

In this method, it is disadvantageous that the presence of a risk of aquaplaning is determined using a characteristic diagram computer. The use of a characteristic diagram computer requires a high degree of expenditure in the application; this is because it is necessary to carry out numerous driving trials with which the individual characteristic diagrams stored in the characteristic diagram computer are determined.

DE 196 08 064 C2 describes a method and a device for determining the grip of wheels in motor vehicles when the underlying surface is not dry. For this purpose, a force acting on at least one wheel is measured permanently. From this measured force, a signal which describes the grip is generated. The force measurement variable is a surge force acting on a wheel in the longitudinal direction of the vehicle when the underlying surface is not dry. A signal which corresponds to that velocity at which the vehicle will aquaplane given the instantaneously present water film thickness is generated from this surge force and from the instantaneous velocity of the vehicle. The surge force is sensed from deformations occurring in the chassis. For this purpose, either travel sensors are provided in elastic bearings in which the transverse link is mounted, as the surge force causes deformations in these bearings via the transverse link, or sensors are used which register the accelerations of the wheel carrier.

A disadvantage with this method is the use of additional sensors which are necessary in order to register the deformations occurring in the chassis.

Against this background, the following object arises: a device for detecting a risk of aquaplaning which occurs during the driving mode of a vehicle is to be provided, in which device the expenditure which is necessary for the application is low and which does not require sensors for registering deformations occurring in the chassis. The same will apply to the method carried out with the device according to the invention.

This object is achieved by means of the features of claim 1 or by means of those of claim 14.

The detection according to the invention of a risk of aquaplaning which occurs during the driving mode of a vehicle, said detection taking place in the device according to the invention in accordance with the inventive method, is based, as an approach, on the law of momentum of the vehicle in the longitudinal direction. From the law of momentum the following equation is obtained.

$$FSW = FA - FLW - FRW - mfzg \cdot (ax - g \cdot \theta) \tag{1}$$

According to this equation, the following forces are taken into account:

The drive forces FA at the driven wheels.

The air resistance force FLW.

The rolling resistance force FRW which results from the shape-changing work at the wheel and underlying surface.

The force $mfzg \cdot (ax - g \cdot \theta)$ resulting from the longitudinal acceleration $ax - g \cdot \theta$ acting on the vehicle. The longitudinal acceleration acting on the vehicle is determined, for example, using a longitudinal acceleration sensor. In this way, the longitudinal acceleration includes two components: a first component ax which is based on the engine torque generated by the engine. A second component $g \cdot \theta$ which includes the gradient $\theta$ of the underlying surface on which the vehicle is located.

The surge resistance force FSW which arises from the fact that on a wet underlying surface the film of water between the tyre and the underlying surface must be expelled. The surge resistance force is usually a force which is directed parallel to the longitudinal axis of the vehicle and which is greater the higher the velocity of the vehicle and the larger the thickness of the water film.

Equation (1) can be interpreted as follows: the first three terms of the right-hand side represent a first propulsion variable which describes the propulsion of the vehicle which is expected on the basis of the operating state of the engine and/or of the drive train. The torque which is output by the engine is transmitted to the driven wheels via the drive train which is composed essentially of the clutch, the gearbox, which may be embodied as a manual shift gearbox or as an automatic gearbox, and the differential gearing. The drive forces FA at the driven wheels result as a function of the rotational speed of the engine, the rotational speeds of the wheels and the respectively set gear speed. A specific value of the velocity of the vehicle is set on the basis of the operating state of the engine and/or of the drive train. On the one hand the air resistance force FLW and on the other the rolling resistance force FRW depend on this value by way of the dependence of the coefficient of rolling resistance on the velocity of the vehicle. It is apparent here that with respect to the propulsion of the vehicle the drive forces at the wheels are reduced by the air resistance force and by the rolling resistance force. In summary, it is possible to state: the expected propulsion of the vehicle can be determined by means of the operating state of the engine and/or of the drive train which is defined by the engine torque, the transmission ratio of the gearbox, the rotational speed of the engine and the rotational speeds of the wheels, as, on the one hand, the drive forces at the driven wheels are predefined by this operating state and, on the other hand, the air resistance force and the rolling resistance force depend on this operating state. Further factors which influence the expected propulsion are not taken into account as they are negligible in comparison with those mentioned above.

The fourth term mfzg·(ax−g·θ) on the right-hand side constitutes a second propulsion variable. It describes the propulsion which is present in the driving mode of the vehicle and which arises due to the longitudinal acceleration ax−g·θ acting on the vehicle. The longitudinal acceleration required for this is registered using a suitable sensor means.

In an ideal case, i.e. when the underlying surface is dry and if no water film forms between the tyres and the underlying surface, the first and second propulsion variables have equally large values. The left-hand term of the above equation, which is referred to as the surge resistance force, has the value zero in this case. If, on the other hand, the underlying surface is wet and as a result a water film forms between the tyres and underlying surface, the first propulsion variable has larger values than the second propulsion variable; this is because in this case the water film must be expelled and there is a surge resistance force which is different from zero. Consequently, the value of the surge resistance force constitutes a measure for an existing water film and thus for a possibly present risk of aquaplaning, and it can thus be evaluated in relation to this.

If there is therefore a deviation between the expected propulsion and the propulsion which arises, the reason for this is a surge resistance force which arises owing to the water film which is formed between the tyre and the underlying surface. Taking this effect as the basis, the following device according to the invention for detecting a risk of aquaplaning which occurs during the driving mode of a vehicle is obtained.

The device according to the invention contains first means which determine a first propulsion variable which describes the propulsion of the vehicle which is to be expected on the basis of the operating state of the engine and/or of the drive train. In addition, the device according to the invention contains second means which determine a second propulsion variable. The latter describes the propulsion which occurs during the driving mode of the vehicle and which arises due to the longitudinal acceleration acting on the vehicle. The presence of the risk of aquaplaning is inferred as a function of a deviation between the first propulsion variable and the second propulsion variable. This deviation represents the surge resistance force described above.

This procedure has the advantage that a risk of aquaplaning which may be present can be detected in a simple way. On the one hand, in contemporary vehicles the variables with which the operating state of the engine and/or of the drive train are described are available via a bus system (CAN bus) contained in the vehicle. On the other hand, the longitudinal acceleration which is necessary for determining the second propulsion variable can easily be made available using a suitable sensor means. Accordingly, it is possible to dispense with the costly characteristic diagram computer known from the prior art. In addition, sensors for registering deformations occurring in the chassis are not required.

Advantageously, third means are provided which determine a deviation variable which describes the deviation between the first propulsion variable and the second propulsion variable As described above, the deviation variable corresponds to the surge resistance force. There is a risk of aquaplaning if the deviation variable is greater than a predefined threshold value or equal to a predefined threshold value.

The threshold value is advantageously determined as a function of the deviation variable and a variable which describes the velocity of the vehicle.

As already stated, the first propulsion variable is composed of three components. In particular these are the following components:

A first component which describes the drive forces which are present at the driven wheels owing to the operating state of the engine and/or of the drive train. This first component is determined as a function of a variable which describes the engine torque, a variable which describes the transmission ratio of the gearbox, a variable which describes the rotational speed of the engine, and variables which describe the rotational speeds of the wheels. By taking into account the rotational speed of the engine and the rotational speeds of the wheels it is possible to perform a dynamic determination of the drive forces. The transmission ratio ig should comprise here all the gearboxes present in the drive train. The drive forces are determined by evaluating the law of conservation of angular momentum applied to the engine and applied to the drive wheels respectively.

A second component which describes the air resistance present during the driving mode of the vehicle. The second component is determined as a function of variables which describe the design and/or the geometry of the vehicle, and a variable which describes the velocity of the vehicle. In a specific case, the second component corresponds to the air resistance force which is determined in accordance with the equation $$FLW = \frac{cLW \cdot \rho \cdot A \cdot vf^2}{2} \qquad (2)$$

The variables used in this equation have the following meaning:
cLW is the coefficient of air resistance of the vehicle,
A is the front face of the vehicle,
ρ is the density of the air, and
vf is the velocity of the vehicle.
The values for the variables cLW and A which constitute the variables which describe the design and/or the geometry of the vehicle, and are thus vehicle-specific, are determined in the foreground within the scope of the application. A constant can be used for the variable ρ.

A third component which describes the rolling resistance present in the driving mode of the vehicle. The third component is determined as a function of a variable which describes the state of the tyres, and a variable which describes the mass of the vehicle. In a specific case, the third component corresponds to the rolling resistance force which is determined in accordance with the equation $$FRW = kRW(vf) \cdot mfzg \cdot g \qquad (3)$$

The variables used in this equation have the following meaning:
kRW(vf) is the variable which describes the state of the tyres. This tyre-specific variable is the coefficient of rolling resistance of the tyres. The coefficient of rolling resistance depends on the variable which describes the velocity of the vehicle and increases as the velocity of the vehicle increases. During the driving mode of the vehicle, the coefficient of friction of the rolling resistance can be read out, for example, from a characteristic curve as a function of the value of the velocity of the vehicle.
mfzg is the mass of the vehicle.
g is the acceleration of the earth.
The determination of the third component becomes more precise if the sum of the individual wheel loads is used instead of the mass of the vehicle. The individual wheel loads are determined, for example, from the spring compression paths determined for the individual wheels. The spring compression paths are in turn present as information if the vehicle has, for example, an active chassis or pneumatic suspension.

The second propulsion variable is determined as a function of a variable which describes the mass of the vehicle and an acceleration variable which describes the longitudinal acceleration acting on the vehicle. The longitudinal acceleration is determined using a suitable sensor means. For this purpose, a longitudinal acceleration sensor by means of which the longitudinal acceleration is measured fixed with respect to the vehicle is advantageously used.

As an alternative to using a longitudinal acceleration sensor, the following procedure is suitable for determining the longitudinal acceleration acting on the vehicle: as already stated above, the longitudinal acceleration acting on the vehicle is composed of two components. The first component ax can be determined from the rotational speeds of the wheels or the velocity of the vehicle. The second component g·θ can be determined using a navigation system. The navigation system knows the position of the vehicle and can make available the gradient of the underlying surface at the respective position using a map which is present in digital form and which contains, inter alia, information on the gradient of the underlying surface.

The gradient of the underlying surface can also be made available using an image processing system with which the profile of the route is evaluated.

With the device according to the invention it is possible to determine the surge resistance force directly from the drive forces at the driven wheels, the velocity of the vehicle and the longitudinal acceleration of the vehicle.

Further influencing factors are advantageously taken into account in the detection of a risk of aquaplaning. For this purpose, various means are provided:

Fourth means which register the state of the road. These means are means for registering the coefficient of friction between the tyres and the underlying surface. As the coefficient of rolling resistance depends on the pairing of tyre and underlying surface, given knowledge of the coefficient of friction it is possible to make available a coefficient of rolling resistance which describes the respective driving mode precisely.

Fifth means which register air movements which are independent of the driving mode of the vehicle. These air movements will be, for example, oncoming wind or tail wind. As these air movements lead to movements of the vehicle body, means are provided for registering them, the individual wheel spring compression paths of the vehicle being evaluated with said means. By taking into account the air movements which are independent of the driving mode, it is possible to determine the air resistance force, and thus ultimately the deviation variable, more precisely.

Sixth means which register the number and/or the type of loads activated during the driving mode of the vehicle. These loads are, for example, a load arranged in a steering system (for example pump of a power steering system) and/or a load arranged in a brake system (for example feedback pump) and/or a load arranged in a light system and/or a load arranged in the interior of the vehicle (for example air conditioning system). The number and/or the type of loads activated during the driving mode of the vehicle are taken into account for the following reason: the loads specified above are generally supplied with electricity by means of the dynamo or driven directly by means of the engine. If a large number of loads are then active during the driving mode, in the first case the dynamo must output a high power level, leading to a situation in which the entire power generated by the engine is no longer available at the driven wheels for the propulsion. The same applies also in the second case. Thus, given knowledge of the number and/or the type of activated loads, it is possible to estimate which proportion of the power generated by the engine is not available for the propulsion. Thus, errors can be reduced in the determination of the drive forces. The power drop which occurs as a result of the activated loads is taken into account using models.

The state of the road and/or the air movements which are independent of the driving mode of the vehicle and/or the number and/or the type of the loads activated during the driving mode of the vehicle are taken into account in the detection of the risk of aquaplaning. As a result of taking the above into account it is possible to determine the deviation variable, i.e. the surge resistance force, more precisely, as a result of which the detection of a risk of aquaplaning becomes more reliable.

The driver is advantageously warned when there is a risk of aquaplaning. However, as it is not ensured that the driver will react to this warning, or if he reacts that he will react correctly and in good time, the information relating to a present risk of aquaplaning is advantageously made available to at least one device for influencing a variable which describes the movement of the vehicle, and is processed in said device. The information made available can be a relative measure of the loss of frictional engagement which occurs owing to the water film located between the tyre and underlying surface. The information is advantageously fed to devices which can reduce the velocity of the vehicle through engine and/or brake interventions. These devices may be, for example, a traction controller or a device for controlling the yaw rate of the vehicle, which is widely known as a vehicle dynamic control or ESP (Electronic Stability Program).

A two-stage procedure is also suitable: for this purpose the deviation variable is compared with a first threshold value and a second threshold value which is larger than the first. If the first threshold value is exceeded, the driver is firstly warned. If the second threshold value is exceeded, measures which reduce the velocity of the vehicle are carried out.

It has proven advantageous that the device according to the invention is equipped with detection means with which it is possible to determine whether or not the underlying surface is wet. This information can be processed as follows: on the one hand it is possible to carry out the detection of the risk of aquaplaning only if the underlying surface is wet. As a risk of aquaplaning can occur only when there is a wet underlying surface, it is also necessary to carry out the detection according to the invention only when the underlying surface is wet. This situation-dependent execution contributes to a situation in which when the underlying surface is dry computational capacity for a detection which is unnecessary in this situation is not linked to a risk of aquaplaning.

On the other hand, the detection of the risk of aquaplaning is also carried out if it is detected that the underlying surface is not wet. That is to say the detection of risk of aquaplaning is carried out permanently, irrespective of whether or not the underlying surface is wet. In this way, when the underlying surface is dry, variables which are taken into account in the detection of the risk of aquaplaning can be determined and/or checked. This determination and/or checking is therefore carried out when the underlying surface is dry as there is no surge resistance force in this situation. As already presented above, the first and the second propulsion variables would ideally have equal values when the underlying surface is dry. However, if there is a deviation between these two propulsion variables, this may be for two reasons. On the one hand, when the sixth means are used to estimate the portion of the power which is generated by the engine and which is not available for propulsion, a deviation from the actual case may occur. In this case, for example the models on which the estimation is based while driving on a dry underlying surface are adapted in such a way that the first and second propulsion variables approximate to one another in terms of value. On the other hand, the third portion which describes the rolling resistance present during the driving mode of the vehicle can deviate from the actual rolling resistance present. The reason for this may be that the state of the tyres has changed during the period of use of the tyre and this state is no longer sufficiently described by the variable which describes the state of the tyres. In this case, while driving on a dry underlying surface the variable which describes the state of the tyres is adapted in such a way that the first and second propulsion variables approximate to one another in terms of value.

With respect to the third portion, it is also conceivable that the pressure of the tyres changes during the period of use of the tyre. A change in the tyre pressure also leads to a change in the rolling resistance. It thus also becomes appropriate, in particular while driving on a dry underlying surface, to check the tyre pressure and if appropriate to adapt the value of the third portion. The checking of the tyre pressure can be carried out with devices which are known from the prior art and which are arranged in vehicles for checking the tyre pressure.

The values which are determined and/or checked when the underlying surface is dry are stored in a memory which is present in the device according to the invention and are thus available if a risk of aquaplaning is to be detected when the underlying surface is wet. As a result, the reliability of the detection according to the invention of a risk of aquaplaning is increased.

The detection means are advantageously a wetness sensor mounted in the region of the vehicle wheels. Alternatively or additionally, the activation of the window wiper and/or the signal of a rain sensor, which serves to adapt the wiping speed of the window wiper automatically to the strength of the rain, can be evaluated.

At this point, the reason why the surge resistance force for detecting a risk of aquaplaning is evaluated will be stated once more: the evaluation of the surge resistance force has a preview function. Significant changes in the surge resistance force occur promptly before a critical loss of frictional engagement, such as occurs in the case of aquaplaning. The risk of aquaplaning can thus be detected early.

Further advantageous refinements can be found in the description and the drawing. The advantageous refinements which emerge from any desired combination of the subclaims will also be included.

Figure 2:
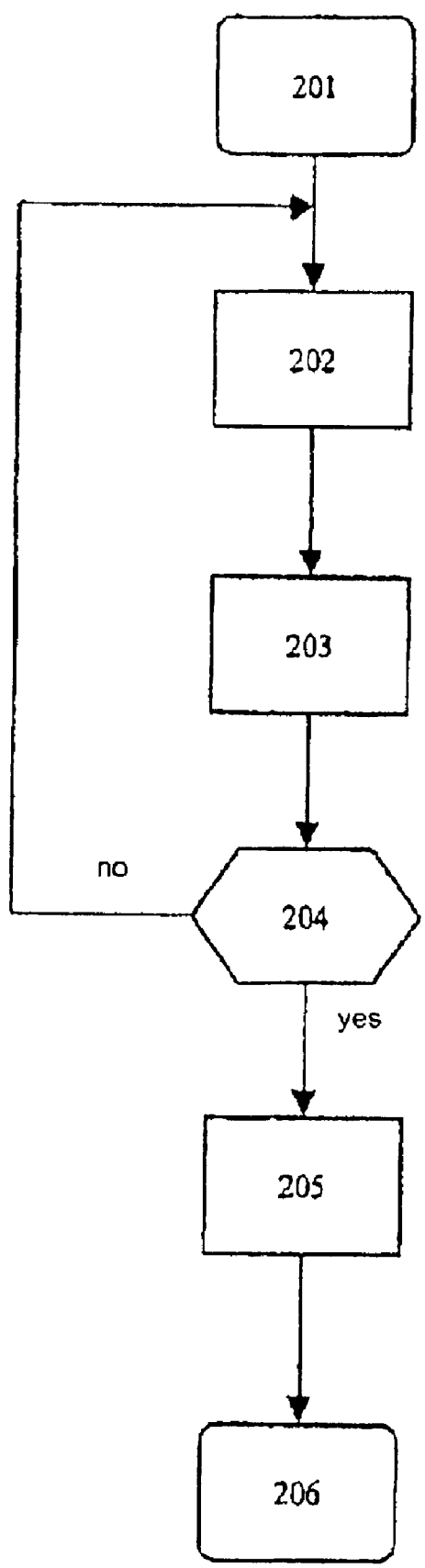

The exemplary embodiment will be described in more detail below with reference to the drawing, in which:

FIG. 1 shows a schematic view of the device according to the invention in the form of a block circuit diagram, FIG. 2 shows a flowchart which is run through in the device according to the invention in order to detect a risk of aquaplaning occurring during the driving mode of a vehicle.

In FIG. 1, first means with which the first propulsion variable vg1 is determined are represented with a block 101.

For this purpose, the block 101 is fed with various signals and/or variables S2 from a block 107. These signals and/or variables comprise a variable Mmot which describes the engine torque, a variable ig which describes the transmission ratio of the gearbox, a variable nmot which describes the rotational speed of the engine, variables nij which describe the rotational speeds of the wheels, a variable vf which describes the velocity of the vehicle and a variable mfzg which describes the mass of the vehicle. The variable vf which describes the velocity of the vehicle is determined in a known fashion from the wheel speeds vij which are obtained in turn from the rotational speeds nij of the wheels. On the basis of equation (1), the first propulsion variable vg1 is determined, for example in accordance with the equation vg1=FA−FLW−FRW. The first propulsion variable vg1 is fed to a block 103.

102 designates second means with which the second propulsion variable vg2 is determined. For this purpose, the block 102 is fed, on the one hand, with a variable mfzg describing the mass of the vehicle from the block 107. On the other hand, the block 102 is fed with a variable ax−g·θ which describes the longitudinal acceleration of the vehicle and which is determined using an acceleration sensor 104. The second propulsion variable which is determined on the basis of equation (1) in accordance with the equation vg2= mfzg·(ax−g·θ) is also fed to the block 103.

The variable which describes the mass of the vehicle is either a permanently predefined variable which was applied in the front area and which is stored, and can thus only represent an estimated variable. Or it is a variable which is determined during the driving mode of the vehicle. This determination does not necessarily have to take place in the block 107. An independent means may also be provided for this.

In the block 103, which represents third means, the deviation variable FSW is determined which describes the deviation present between the first and second propulsion variables. This takes place, for example, in accordance with the above equation (1). As already stated, the deviation variable is the surge resistance force FSW. The deviation variable FSW is compared with an associated threshold value. If the deviation variable FSW is greater than this threshold value, or is equal to this threshold value, there is then a risk of aquaplaning, and a variable aquaplgef is output to a block 106 and to the block 107.

The block 106 is a warning means which warns the driver about the risk of aquaplaning if said means are informed by the variable aquaplgef that there is a risk of aquaplaning. The warning can be effected either visually or audibly.

Fourth means 105a, fifth means 105b and sixth means 105c are combined to form a block 105. The state of the road is registered with the fourth means. For this purpose, the coefficient of friction between the tyre and the underlying surface is determined. Air movements which are independent of the driving mode of the vehicle are registered with the fifth means. For this purpose, the individual wheel spring compression paths of the vehicle are evaluated. With the sixth means, the number and/or the type of loads activated during the driving mode of the vehicle is registered. The information obtained with the means 105a, 105b and 105c are fed to the block 103 using the signals or variables S1.

The means 105a, 105b and 105c which are stated above, and thus the variables S1 which are determined with them, are not necessarily required for the execution of the detection of the risk of aquaplaning according to the invention. However, they can be used to improve the detection. Against this background, the device according to the invention does not need to contain these three means, or does not need to contain all three means simultaneously. A single means or any desired number of these three means may be used.

The block 110 is a detection means used to detect whether or not the underlying surface is wet. For this purpose, this detection means can be embodied as a wetness sensor which is mounted in the region of the vehicle wheels. The wetness sensor operates in such a way that it outputs a signal as soon as at least part of its measuring surface is covered with liquid. The greater the application of liquid, the greater the value of the signal which is output by it. As an alternative to or in addition to using a wetness sensor, it is conceivable to evaluate, in the determining means 110, the activation of the window wiper or the signal which is generated by a rain sensor.

The signal nasserk which is generated with the determining means 110 is fed to the blocks 103 and 107. If the information that the road is dry is present in the block 103, the deviation variable is, for example, not determined or not output. If the information that the road is dry is present in the block 107, the signals or variables S2, for example, are not output. Alternatively, when the underlying surface is dry, it is possible to continue the detection of the risk of aquaplaning according to the invention and to use the detection for checking or determining variables which are included in this detection.

In addition, in the event of the variable which describes the mass of the vehicle being determined during the driving mode of the vehicle, the following procedure is conceivable: as long as the underlying surface is dry, the mass of the vehicle is regularly determined at specific time intervals. As soon as the underlying surface is wet, the last value determined for the mass of the vehicle is frozen. No new value is determined any more.

The block 107 is a regulator means which, together with the associated actuator system 108 and sensor system 109, forms a device for influencing a variable which describes the movement of the vehicle.

This device—to be more precise the regulator means 107—is supplied, by the device according to the invention, with the information relating to a risk of aquaplaning, using the signal aquaplgef. In the regulator means 107, this information is processed to the effect that, when there is a risk of aquaplaning, suitable measures for reducing the velocity of the vehicle are taken. To do this, for example engine interventions and/or brake interventions are carried out independently of the driver.

Using the signals or variables S5, the regulator means 107 is supplied, from the sensor system 109, with the input variables which are necessary for carrying out the regulating method implemented in the regulator means 107. In accordance with the implemented regulating method, the regulator means 107 generates signals S3 which are fed to the actuator system 108 for regulating the variable which describes the movement of the vehicle and which is to be regulated using the regulating method. From the actuator system 108, the regulator means 107 receives, by means of the signals or variables S4, an acknowledgement relating to the operating state of the individual actuators combined to form the actuator system 108.

If there is then a risk of aquaplaning, either signals or variables with which the velocity of the vehicle is decreased in order to reduce the risk of aquaplaning are output instead of the signals or variables which are generated and output by the regulator means 107 in accordance with the regulating method implemented in it in order to regulate the variable describing the movement of the vehicle, or else modified signals or variables are output.

The present device which is composed of the regulator means 107, the actuator system 108 and the sensor system 109 can be, for example, a drive slip controller with which the drive slip occurring at the individual wheels of the vehicle is controlled. In this case, the sensor system 109 comprises a pedal value generator with which the actuation of the accelerator pedal by the driver can be determined, and sensors for the rotational speed of the wheels. Alternatively, it can be a device for regulating the yaw rate of the vehicle. In this case, the sensor system 109 comprises sensors for the rotational speed of the wheels, a steering angle sensor, a transverse acceleration sensor, a yaw rate sensor, a sensor for registering the pilot pressure set by the driver, and also the pedal value generator mentioned above.

FIG. 2, in which the sequence of the method according to the invention is illustrated by means of a flowchart, will be described below.

The method according to the invention starts with a step 201 followed by a step 202. In step 202, the output variables which are required to detect the risk of aquaplaning occurring during the driving mode of the vehicle are made available. The variables concerned are the variable Mmot which describes the engine torque, the variable ig which describes the transmission ratio of the gearbox, the variable nmot which describes the rotational speed of the engine, the variables nij which describe the rotational speed of the wheels, the variable mfzg which describes the mass of the vehicle, the variable vf which describes the velocity of the vehicle and the variable $ax-g\cdot\theta$ which describes the longitudinal acceleration of the vehicle.

Step 202 is followed by step 203 in which the deviation variable FSW is determined. This is carried out, for example, using the equations (1), (2) and (3) stated above.

Step 203 is followed by step 204 in which it is determined whether or not a risk of aquaplaning occurs during the driving mode of the vehicle. For this purpose, the deviation variable FSW is compared with an associated threshold value. If it is detected during this comparison that the deviation variable is greater than or equal to the associated threshold value, which is equivalent to there being a risk of aquaplaning, a step 205 is carried out following the step 204. If, on the other hand, it is determined that the deviation variable is smaller than the associated threshold value, which is equivalent to there being no risk of aquaplaning, step 202 is carried out again following step 204.

In step 205, as there is a risk of aquaplaning, the driver is warned, or measures for reducing the velocity of the vehicle are taken by a device with which a variable which describes the movement of the vehicle is influenced. Following step 205, step 206 is carried out, with which the method according to the invention ends.

The threshold value with which the deviation variable is compared can, in the simplest case, be a permanently predefined value which has been applied in the front area. However, the threshold value is advantageously determined during the driving mode of the vehicle since the threshold value should be adapted to the respective existing driving situation. The threshold value which is adapted to the driving mode is determined in step 203 or in block 103. For this purpose, the velocity vf of the vehicle is fed to the block 103 from the block 107.

The threshold value is determined as follows: the value of the surge resistance force is known. Likewise, the value of the velocity vf of the vehicle is known. A point on a curve which describes the dependence of the surge resistance force on the velocity of the vehicle is defined by these two values. In the region which is relevant for the determination of the threshold value, this profile can be approximated by a linear function whose gradient is known from the application. In the application, or by means of empirical determination, a limit curve has been determined which describes the profile of the maximum values of the surge resistance force for different depths of water as a function of the velocity of the vehicle. The maximum value of the surge resistance force is the value of the surge resistance force which is present at the velocity of the vehicle at which the aquaplaning occurs. For the respective operating state of the vehicle, the maximum value of the surge resistance force which applies to it is obtained as an intersection point of the linear function with the limit curve. This maximum value of the surge resistance force is used as a threshold value.

In the comparison of the deviation variable with the threshold value, it is possible to compare the value of the deviation variable with the threshold value. In order to detect whether there is a risk of aquaplaning, it is thus possible to check whether the surge resistance force is greater in terms of value than or equal to the threshold value. In order to obtain a safety margin, the comparison can be carried out with a reduced threshold value which is reduced by a predefined value from the maximum value.

It is also appropriate to check whether the deviation variable exceeds a predefined percentage of the threshold value.

The detection of a risk of aquaplaning according to the invention can also be carried out during a braking operation. For this purpose, the braking forces present on the wheels have to be taken into account. The individual braking forces can be determined, for example, from the individual brake pressures present at the wheels. If the vehicle is equipped with an electrical hydraulic brake system, for example, the brake pressures can be determined using pressure sensors assigned to the individual wheel brakes.

To conclude, it is to be noted that the representation chosen in the description, or that chosen in the drawing, is not intended to have a restrictive effect on the idea which is essential to the invention.

What is claimed is:

1. Device for detecting a risk of aquaplaning which occurs during the driving mode of a vehicle, the device containing for this purpose
   first means (101) which determine a first propulsion variable (vg1) which describes the propulsion of the vehicle which is to be expected on the basis of the operating state of the engine and/or of the drive train, and
   second means (102) which determine a second propulsion variable (vg2) which describes the propulsion which occurs during the driving mode of the vehicle and which arises due to the longitudinal acceleration (ax–g·θ) acting on the vehicle,
   the presence of the risk of aquaplaning being inferred as a function of a deviation between the first propulsion variable (vg1) and the second propulsion variable (vg2).

2. Device according to claim 1, characterized in that third means (103) are provided which determine a deviation variable (FSW) which describes the deviation between the first propulsion variable (vg1) and the second propulsion variable (vg2), there being a risk of aquaplaning if the deviation variable is greater than a predefined threshold value.

3. Device according to claim 2, characterized in that the threshold value is determined as a function of the deviation variable and a variable (vf) which describes the velocity of the vehicle.

4. Device according to claim 1, characterized in that the first propulsion variable (vg1) is composed of the following components:
   a first component (FA) which describes the drive forces which are present at the driven wheels owing to the operating state of the engine and/or of the drive train, and
   a second component (FLW) which describes the air resistance present in the driving mode of the vehicle, and/or
   a third component (FRW) which describes the rolling resistance present in the driving mode of the vehicle.

5. Device according to claim 4, characterized in that the first component is determined as a function of a variable (Mmot) which describes the engine torque, a variable (ig) which describes the transmission ratio of the gearbox, a variable (nmot) which describes the rotational speed of the engine, and variables (nij) which describe the rotational speeds of the wheels, and/or
   in that the second component is determined as a function of variables (cLW, A) which describe the design and/or the geometry of the vehicle, and a variable (vf) which describes the velocity of the vehicle, and/or in that the third component is determined as a function of a variable (kRW(vf)) which describes the state of the tyres, and variable (mfzg) which describes the mass of the vehicle.

6. Device according to claim 5, characterized in that the variable which describes the state of the tyres is the coefficient of rolling resistance (kRW(vf)) of the tyres, in particular the latter is determined as a function of the variable which describes the velocity of the vehicle.

7. Device according to claim 1, characterized in that the second propulsion variable (vg2) is determined as a function of a variable (mfzg) which describes the mass of the vehicle and an acceleration variable (ax–g·θ) which describes the longitudinal acceleration acting on the vehicle.

8. Device according to claim 7, characterized in that the acceleration variable is registered using a sensor means (104), in particular a longitudinal acceleration sensor, or
   in that the acceleration variable is determined as a function of variables (nij) which describe the rotational speeds of the individual wheels or a variable (vf) which describes the velocity of the vehicle, and as a function of a variable which describes the gradient (θ) of the underlying surface and which is made available in particular by a navigation system.

9. Device according to claim 1, characterized in that fourth means (105a) which register the state of the road and/or
   fifth means (105b) which register air movements which are independent of the driving mode of the vehicle, and/or
   sixth means (105c) which register the number and/or the type of loads activated during the driving mode of the vehicle, are provided, and in that the state of the road and/or the air movements which are independent of the driving mode of the vehicle and/or the number and/or the type of the loads activated during the driving mode of the vehicle are taken into account in the detection of the risk of aquaplaning.

10. Device according to claim 1, characterized in that the fourth means (105a) are means for registering the coefficient of friction between the tyres and the underlying surface, and/or
    in that the fifth means (105b) are means which evaluate the individual wheel spring compression paths of the vehicle, and/or in that the loads activated during the driving mode are a load arranged in a steering system and/or a load arranged in a brake system and/or a load arranged in a light system and/or a load arranged in the interior of the vehicle.

11. Device according to claim 1, characterized in that the driver is warned when there is a risk of aquaplaning (aquaplgef, 106), and/or in that the information (aquaplgef) relating to a present risk of aquaplaning is made available to at least one device (107, 108, 109) for influencing a variable which describes the movement of the vehicle and is processed in said device, in particular when there is a risk of aquaplaning, engine interventions and/or brake interventions are carried out in order to reduce the velocity of the vehicle.

12. Device according to claim 1, characterized in that detection means (110) are provided which detect whether there is a wet underlying surface, and in that the detection of the risk of aquaplaning is carried out if it is detected that there is a wet underlying surface, or in that the detection of the risk of aquaplaning is carried out even if it is detected that the underlying surface is not wet, in which case variables which are taken into account in the detection of the risk of aquaplaning are determined and/or checked.

13. Device according to claim 12, characterized in that the detection means are a wetness sensor mounted in the region of the vehicle wheels and/or in that the activation of the window wiper and/or the signal of a rain sensor arranged in a window wiper system is evaluated in the detection means.

14. Method for detecting a risk of aquaplaning which occurs during the driving mode of a vehicle, in which a first propulsion variable (vg1) is determined which describes the propulsion of the vehicle which is to be expected on the basis of the operating state of the engine and/or of the drive train, and in which a second propulsion variable (vg2) is determined which describes the propulsion which occurs during the driving mode of the vehicle and which arises due to the longitudinal acceleration acting on the vehicle, the presence of the risk of aquaplaning being inferred as a function of a deviation between the first propulsion variable (vg1) and the second propulsion variable (vg2).

* * * * *